(12) United States Patent
Graf et al.

(10) Patent No.: US 9,188,464 B2
(45) Date of Patent: Nov. 17, 2015

(54) SENSING DEVICE

(75) Inventors: Markus Graf, Zurich (CH); Pascal Gerner, Zurich (CH); Christian Landis, Hombrechtikon (CH); Matthias Streiff, Zurich (CH)

(73) Assignee: Sensirion AG, Stafa (CH)

( * ) Notice: Subject to any disclaimer, the term of this patent is extended or adjusted under 35 U.S.C. 154(b) by 162 days.

(21) Appl. No.: 13/992,079

(22) PCT Filed: Dec. 16, 2011

(86) PCT No.: PCT/CH2011/000301
§ 371 (c)(1),
(2), (4) Date: Aug. 2, 2013

(87) PCT Pub. No.: WO2012/083470
PCT Pub. Date: Jun. 28, 2012

(65) Prior Publication Data
US 2013/0305822 A1 Nov. 21, 2013

(30) Foreign Application Priority Data
Dec. 22, 2010 (EP) ..................... 10015937

(51) Int. Cl.
*G01D 11/24* (2006.01)
*G01N 25/56* (2006.01)
*G01N 27/04* (2006.01)
*G01N 27/22* (2006.01)
*H04Q 9/00* (2006.01)

(52) U.S. Cl.
CPC .............. *G01D 11/245* (2013.01); *G01N 25/56* (2013.01); *G01N 27/048* (2013.01); *G01N 27/223* (2013.01); *H04Q 9/00* (2013.01); *H04Q 2209/43* (2013.01); *H04Q 2209/84* (2013.01); *Y10T 29/49002* (2015.01)

(58) Field of Classification Search
CPC ...................................... G01D 11/24
USPC .............................................. 73/431
See application file for complete search history.

(56) References Cited

U.S. PATENT DOCUMENTS

| 8,007,167 | B2 * | 8/2011 | Cummins .................. 374/16 |
| 2008/0227235 | A1 * | 9/2008 | Theuss et al. .............. 438/53 |
| 2008/0250847 | A1 * | 10/2008 | Kitani et al. ............. 73/31.05 |
| 2008/0285633 | A1 * | 11/2008 | Rofougaran .............. 375/219 |

FOREIGN PATENT DOCUMENTS

| WO | 2007/036922 | 4/2007 |
| WO | WO 2007036922 A1 * | 4/2007 |

OTHER PUBLICATIONS

"C701 802.15.4 Zigbee-Ready Wireless Sensor Module", Cratlon Electronics R & D, Sep. 9, 2004, XP002413991, 1 page.
PCT International Search Report in connection with PCT/CH2011/000301, completed on Jul. 2, 2012 and mailed Jun. 6, 2012.

* cited by examiner

*Primary Examiner* — Lisa Caputo
*Assistant Examiner* — Jamel Williams
(74) *Attorney, Agent, or Firm* — Cooper & Dunham LLP

(57) ABSTRACT

The present sensing device comprises a sensor (1, ) for providing sensor data representative of a quantity to be measured. Together with the sensor (1, ) a radio frequency interface (2, ) for transmitting the sensor data is arranged in a casing (3, ). The casing (3, ) comprises an opening (33, ) for exposing a sensitive element (11, ) of the sensor (1, ) to an environment of the casing (3, ). A seal (4, ) is provided for sealing the opening (33, ) against an interior (3, ) of the casing (3, ). The sensing device can be used as autonomous humidity detector for detecting humidity e.g. in cars under test.

10 Claims, 2 Drawing Sheets

SENSING DEVICE

CROSS REFERENCES TO RELATED APPLICATIONS

This application is a §371 national stage of PCT International Application No. PCT/CH2011/000301, filed Dec. 16, 2011, claiming priority of European Patent Application 10 015 937.5, filed Dec 22, 2010, the entire contents of each of which are hereby incorporated by reference into this application in its entirety.

TECHNICAL FIELD

The present idea refers to a sensing device and to a method for manufacturing a sensing device.

BACKGROUND ART

Subject to the application and the quantity to be measured sensors may need to be arranged at locations that may be difficult to access. Installing a cabling for connecting such sensors may be cumbersome and may result in a considerable technical effort and/or investment.

DISCLOSURE OF THE INVENTION

The problem to be solved by the present invention is therefore to provide a sensing device with an exposed sensitive element which sensing device may be easily installed in environments which are difficult to access.

According to a first aspect of the present invention, a sensing device is provided with a sensor for providing sensor data representative of a quantity to be measured, and a radio frequency interface for transmitting the sensor data. Such sensing device provides a casing for the sensor and the radio frequency interface, the casing comprising an opening for exposing a sensitive element of the sensor to an environment of the casing. A seal is arranged for sealing the opening against an interior of the casing.

The sensing device is autonomous in that it does not need any cabling and is protected from the environment such that it can be installed in an exposed manner in even hardly accessible environments. Especially, the sensing device may be implemented such that it is also autonomous from a local energy source such as batteries: When the radio frequency interface is implemented in transponder technology, an external reader may initiate a wireless transfer of energy for operating the sensor and the radio frequency interface. In this sense, not only data communication is provided wirelessly between the sensing device and the reader but also the energy transfer from the reader to the device. The sensing device may be interpreted as a tag to be attached to its destination which tag provides sensor data representative of the quantity of the desired measure when being energized. Still, the sensor is protected by the casing including an appropriate seal between the interior and the opening in the casing. As such, the sensor device is easily mountable, requires only little space, and may be used in test applications where measures may need to be taken at multiple locations. The tag may also be mounted permanently in other applications and transmit sensor data on demand, i.e. when being energized from the outside. In case the casing at least partly makes use of low cost plastic foils the sensing device can be manufactured economically and adapts to the shape of the electronics in the interior which supports a small form factor of the device.

The opening in the casing can be arranged in different parts of the casing. The casing may advantageously comprise a support for holding the sensor and the interface, and a cover. Support and cover may represent any two casing elements together forming the casing with or without additional casing elements. The support typically is defined as casing element the sensor is arranged at. When the opening granting access to the sensitive element of the sensor is arranged in the support, a sensor chip including the sensor and possibly other electronics may be flip chip mounted on the support. Then, the sensor preferably covers the opening with its sensitive element facing the opening. On the other hand, when the opening is included in the cover, the sensor may be mounted on the support without being flipped, i.e. with the sensitive element and possibly other electronics integrated facing the cover. For the reason that in such embodiment the sensor chip is mounted with its back side to the support, through-silicon vias may be provided in the sensor chip to establish an electrical connection from the sensitive element and the electronics on a front side of the sensor chip to contact pads on a back side of the sensor chip. In another embodiment, instead of using through-silicon vias, bond wiring may be applied to the sensor chip providing an electrical connection from the front side of the sensor chip to the conducting paths on the support.

According to another aspect of the present invention, a method for manufacturing a sensing device is provided. A sensor for providing sensor data representative of a quantity to be measured and a radio frequency interface for transmitting the sensor data are arranged on a support of a casing for the sensor and for the radio frequency interface. An opening of the casing for exposing a sensitive element of the sensor to an environment is sealed against an interior of the casing. The interior is closed with a cover.

Other advantageous embodiments of both the sensor device and the method are listed in the dependent claims as well as in the description below.

The advantageous embodiments similarly pertain to the apparatus and to the method. Synergetic effects may arise from different combinations of the embodiments although they might not be described in detail.

Further on it shall be noted that all embodiments of the present invention concerning a method might be carried out in the order of the steps as described or in any other order. The disclosure and scope of the invention shall include any order of steps irrespective of the order listed in the claims.

BRIEF DESCRIPTION OF THE DRAWINGS

The aspects defined above and further aspects, features and advantages of the present invention can also be derived from the examples of embodiments to be described hereinafter and are explained with reference to Figures of such embodiments.

MODES FOR CARRYING OUT THE INVENTION

Figure 1:
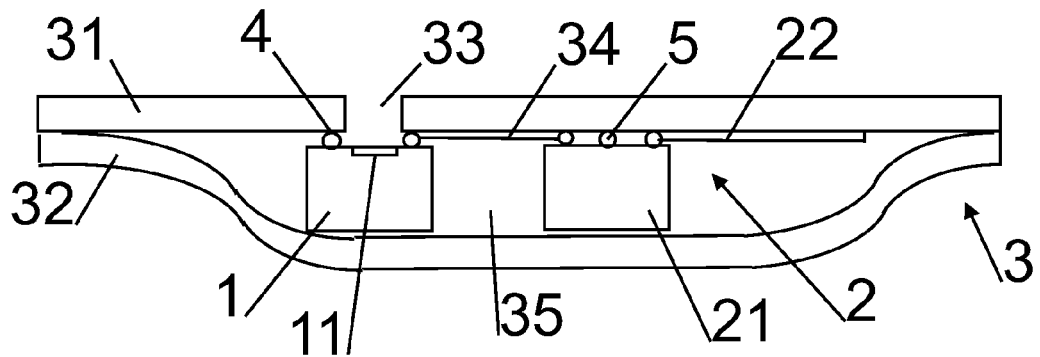
FIG. 1 shows a longitudinal cut of a sensing device according to an embodiment of the present invention.

Similar or relating components in the figures are provided with the same reference numerals. The view in the figures is schematic and not fully scaled.

FIG. 1 shows a longitudinal cut of a sensing device according to an embodiment of the present invention. In the present example, the sensing device represents a humidity detector comprising a sensor 1 in form of a humidity sensor. The humidity sensor 1 is embodied as a sensor chip comprising a sensitive element 11 which in the present example may be a polymer layer receptive to humidity. The polymer layer may interact with electrodes in the sensor chip such that by capacitive sensing any change in the dielectric properties of the polymer layer evoked by humidity in the environment of the sensor 1 may be detected.

In the present example, the sensor 1 is mounted to a support 31 of a casing 3 for the sensor 1. The support 31 comprises an opening 33 which faces the sensitive element 11 of the sensor 1 such that the sensor 1 is enabled to detect the humidity prevailing in an environment outside the casing 3. At least, the sensitive element 11 is coupled to the opening 33 such that access to the measure may be granted. The sensor 1 is flip chip mounted to the support 31 such that the sensor chip faces the support 31 with its sensitive element 11. Next to the sensitive element 11, electronic circuitry may be provided and integrated in the sensor chip on the same front side facing the support 31. Solder or other kind of conducting bumps provided between contact pads on the front side of the sensor chip and contact pads on the support 31 arrange for an electrical connection to conductor paths 34 arranged on the support 31. In the present example, such solder bumps also provide for the mechanical mounting of the sensor chip to the support 31.

In addition to the sensor 1, a radio frequency interface 2 is arranged on the support 31. In the present example, the radio frequency interface 2 comprises an antenna 22 arranged on the support 31 and an integrated radio frequency interface chip 21 providing electronic circuitry for supporting the interface functions. The interface chip 21 is flip chip mounted to the support 31 by means of solder bumps 5 arranged between contact pads on a front side of the interface chip 21 carrying the electronic circuitry and contact pads on the support 31 which solder bumps 5 electrically and mechanically connect the interface chip 21 to the conductor paths 34 of the support 31 and to the antenna 22.

The support 31 may be embodied as a flexible foil made from plastics such as PET with the conducting elements such as the conductor paths 34, the antenna 22 and the contact pads and/or other electrical elements printed thereon or attached thereto. Alternatively, the support 31 may be embodied as a flexible printed circuit board, or as a non-flexible printed circuit board.

A cover 32 is provided for closing an interior 35 of the casing 3. The sensor 1 and the radio frequency interface 2 are arranged in the interior 35 of the casing 3 which interior 35 is defined by the support 31 and the cover 32. The cover 32 preferably is embodied as a flexible foil made from plastics such as PET. In its periphery, the cover 32 may be glued or bonded to the support 31 such that this mechanical interface provides for a water-tight and/or gas-tight seal subject to the application of the sensing device. By means of the flexible cover 32, the casing 3 may be adapted in shape to the components in the interior 35 and as a result only claim little space. The interior 35 may be filled by air, or may be filled by a semi-solid or a solid compound. In a preferred embodiment, the interior 35 may be filled by one of a polymer, an adhesive, or a film. In case the sensor 1 is embodied as a humidity sensor and the sensitive element 11 is sensitive to humidity, complete or partial filling of the interior 35 may prevent from having a micro climate developed in the interior 35.

The radio frequency interface 2 is adapted for transmitting data in the radio frequency range—preferably in the high frequency range of 10 kHz to 10 GHz to some external receiver by means of the antenna 22. Such data preferably is data received from the sensor 1 which sensor data preferably provides information about the relative humidity in the present example. Such sensor data may already be digitized in the sensor 1 and be provided as digital value to the radio frequency interface 2. In addition, the radio frequency interface 2 may be embodied to transmit an identifier for identifying the present sensing device and distinguish it from other sensing devices.

In a very preferred embodiment, the radio frequency interface 2 comprises means for deriving energy from a signal received by the antenna 22 of the radio frequency interface 2 for operating the sensor 1 and for operating the radio frequency interface 2. Such means may comprise a rectifier for converting AC into DC and a storage capacity. As such, the sensing device in an advantageous embodiment is a passive component without any energy source including any battery. In such scenario, the interface 2 preferably comprises a transponder similar to the ones used in the Radio Frequency Identifier RFID technology which when exposed to an electric field of a reader is energized and reacts by transmitting data such as the sensor data and the identification to the reader. In this context, any data communication between the external reader and the sensing device preferably may be bidirectional in a wireless way. An energy transfer is performed by the reader to the sensing device in a wireless way. Still, in another embodiment, the sensing device may comprise one or more active components such as a battery for supplying the sensor 1 and the radio frequency interface 2 with energy from within the sensing device rather than from the outside.

In any of these scenarios, the sensing device can wirelessly interact with a remote reader for reading the sensor data from the sensing device which reader preferably is adapted to receive and identify the sensor data possibly along with other information such as an identifier of the sensing device. In case the sensing device is a passive component, the reader energizes the sensing device and reads out the sensor data during such energizing period.

For the reason that the sensing device shall reliably be operated in any environment, all mechanical interfaces comprised in the casing 3 advantageously are sealed against splash water. In another embodiment, the mechanical interfaces may be embodied to prevent a condensate from entering the interior 35, especially, when the sensing device is embodied as humidity sensing device. Hence, a seal 4 is provided for sealing the opening 33 against the interior 35 of the casing 3. The seal 4 may be preferably be embodied as a functional polymer or as a sealing adhesive. In some embodiments, the sealing device may even be embodied as an O-ring made from rubber. In the present example, the seal 4 is built by the solder bumps also used for electrically and mechanically connecting the sensor 1 to the support 2. An underfill may be used for enhancing the mechanical stability of the connection. In another preferred embodiment, an adhesive connection may be used, e.g. in the form of an Anisotropic Conductive Adhesive (ACA) or a Non Conductive Adhesive (NCA). Such connection may simultaneously provide the electrical connection and mechanical stability. For such connection, the chip is prepared by arranging conducting bumps on the contact pads of the chip. The adhesive typically is arranged on the chip not only around the bumps but also in other areas for providing good mechanical stability. In the present example, the adhesive, of course, would not cover the sensitive element 11 or other parts of the chip surface facing the opening 33.

Subsequently, the chip is pressed against the support 31. When the adhesive hardens it shrinks such that the bumps are drawn into the contact pads on the support and provide for an electrical connection in combination with mechanical stability. The adhesive in the first embodiment may comprise few conducting particles which enhance the electrical connection only at the contact between the bump and the contact pad while the non conducting adhesive does not include such particles. The bumps advantageously are made from gold by cutting a golden bond wire after connecting it to the contact pad of the chip.

The tag-like sensing device can easily be used and attached in/to any locations that are difficult to access. No cabling is required and due to its small size the sensing device may also be installed in small compartments. For attaching the sensing device to a mounting location it is preferred that either the cover 32 may be provided with an adhesive layer at its outside surface, or the support 31 may be provided with an adhesive at its outside surface such that the sensing device may simply be glued to the mounting location. However, in case the outside surface of the support 31 is used to mount the sensing device to its destination, care needs to be taken that the opening 33 still provides sufficient access to the environment. In another preferred embodiment, an absorbing layer made from metal is attached to the outside surface that will be facing the mounting destination. An adhesive in turn may be attached to the absorbing layer for mounting the tag. When mounting the tag to a metal destination, a magnetic flux issued by the reader may induce currents into the metal destination. Such induced currents in turn may invoke a magnetic field which may impair the electromagnetic field of the reader and as such cause malfunctions in the communication between the tag and the reader. The magnetic layer may reduce or cancel this effect.

Figure 2:
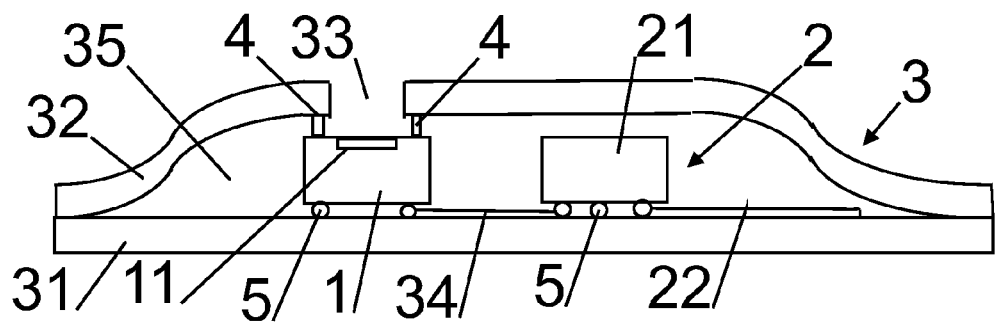
FIG. 2 shows a longitudinal cut of a sensing device according to another embodiment of the present invention.

FIG. 2 shows a longitudinal cut of a sensing device according to another embodiment of the present invention. This embodiment differs from the embodiment in FIG. 1 in that the opening 33 is arranged in the cover 32 instead of in the support 31. This in turn requires the sensitive element 11 not to face the support 31 but to face the opening 33 in the cover 32. Accordingly, the sensitive element 11 and any electronic circuitry are arranged at a front side of the sensor chip which faces the cover 32. In order to provide an electrical connection between the sensor 1 and the support 31 the present sensor chip comprises contact pads on the back side which are soldered by means of solder bumps 5 to contact pads on the support 31. For connecting the sensitive element 11 and the circuitry on the front side of the sensor chip to the contact pads on its back side through-silicon vias are provided in the sensor chip which constitute an electrical connection through the depth of the sensor chip. For the interface chip 21 there is no modification needed compared to the embodiment of FIG. 1. It still may be flipped and mounted with its front side comprising the circuitry to the support 31 in a flip chip manner.

Figure 3:
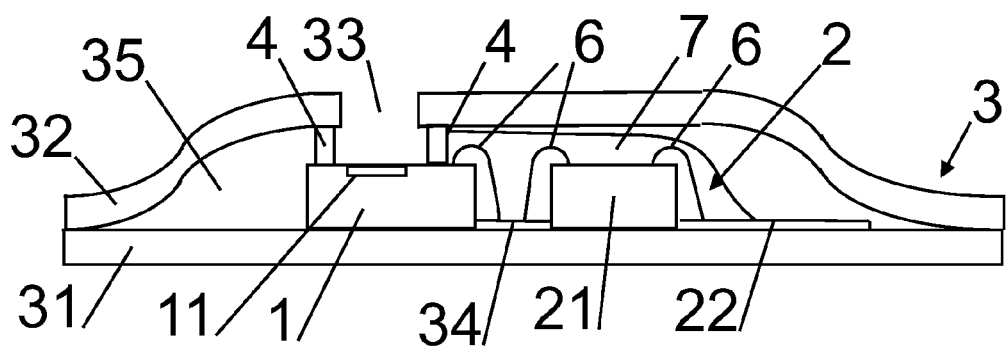
FIG. 3 shows a longitudinal cut of a sensing device according to a third embodiment of the present invention.

FIG. 3 shows a longitudinal cut of a sensing device according to another embodiment of the present invention. This embodiment differs from the embodiment in FIG. 2 in that no longer flip chip mounting technology is used but wire bonding for electrically contacting the sensor chip and the interface chip 21 to the support 31. Both of the chips are arranged on the support 31, e.g. glued to the support 31. Wire bonding is applied to the front sides of the chips. The bond wires are enclosed by a compound 7 prior to closing the casing 3 by means of the cover 32.

The seal in FIGS. 2 and 3 may again be one of a sealing adhesive, a functional polymer, a rubber O-ring, solder bumps, or a combination of bumps and adhesive. In the embodiments of FIGS. 2 and 3, advantageously an adhesive layer for attaching the sensing device to its destination is provided on the outside surface of the support 31.

Figure 4:
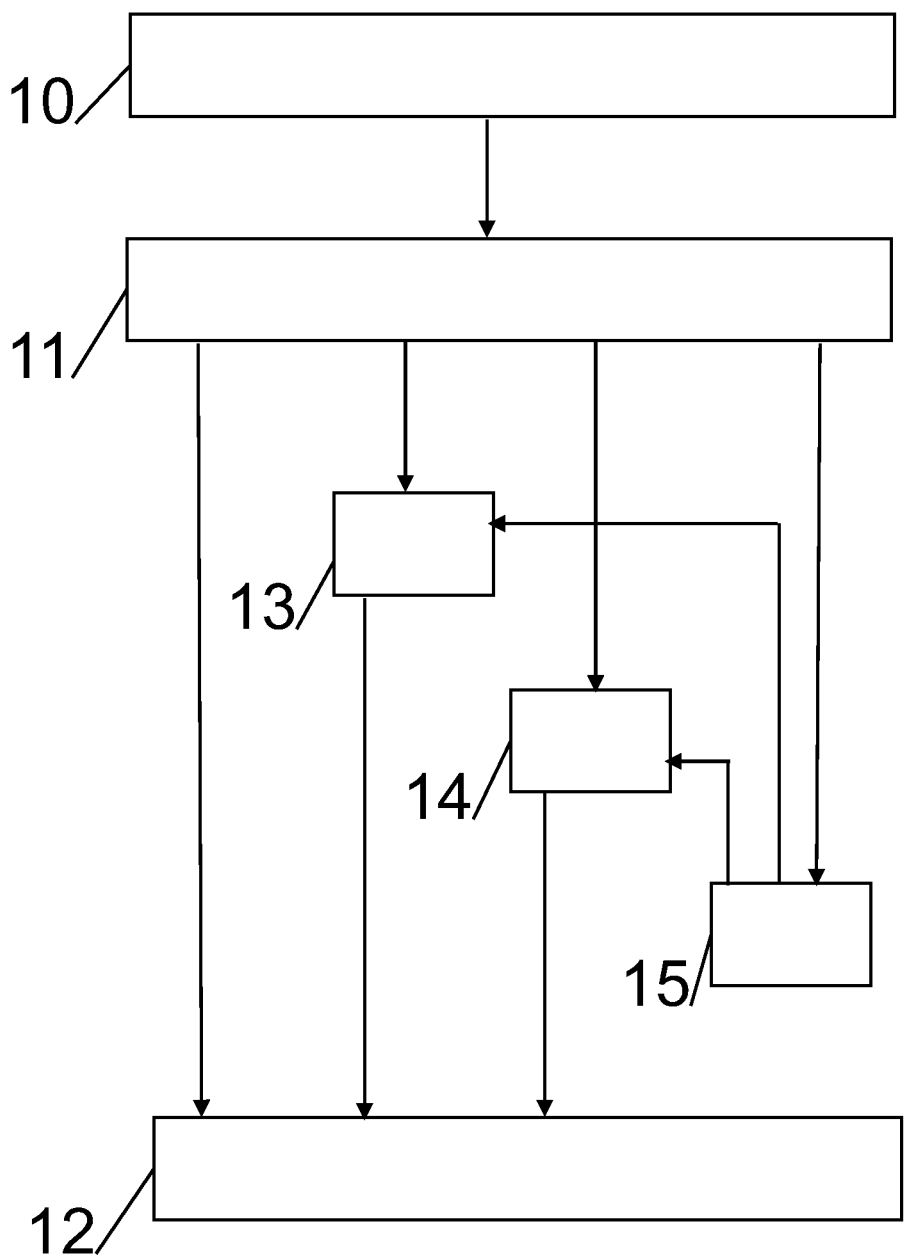
FIG. 4 shows a flow chart illustrating a method for manufacturing a sensing device according to an embodiment of the present invention.

FIG. 4 shows a flow chart illustrating a method for manufacturing a sensing device according to an embodiment of the present invention. In step 10 a support is provided with a layout provided thereon comprising conductor paths and possibly the antenna of the radio frequency interface, and contact pads. Such support may be prefabricated. In step 11 a sensor for providing sensor data representative of a quantity to be measured and a radio frequency interface for transmitting the sensor data are arranged on the support at the desired positions. In a first embodiment, such arrangement includes arranging the sensor on top of an opening in the support. In this embodiment such arrangement also includes providing the mechanical and electrical connection between the sensor and the support as illustrated in connection with FIG. 1, for example. The sensor chip and the interface chip may be prepared with solder bumps at their contact pads to be ready to be pressed against the contact pads of the support. In such embodiment, the solder bumps may simultaneously build the seal between the opening and the sensor. Alternatively, the sealing material may be attached to the cover around the opening. Finally, a cover is attached to the support in step 12 by that building a casing for the sensor and the interface and by that closing the interior of the casing.

In an alternative embodiment, the cover includes the opening. In such scenario, the arrangement of step 11 includes providing the mechanical and electrical connection between the sensor and the support, as illustrated in connection with FIG. 2, for example. In step 13 a sealing material is attached to the sensor. Alternatively, in step 14 the sealing material is attached to the cover around the opening. Finally, in both alternatives, the cover is attached to the support in step 12 by that building a casing for the sensor and the interface. By means of pressing the cover against the sensor, the seal between the opening and the interior becomes effective.

In another embodiment, the arrangement of step 11 includes providing only the mechanical connection between the sensor and the support, as is illustrated in connection with FIG. 3, for example. In such scenario, in step 15 the electrical connection is provided, for example, by means of wire bonding and moulding the bond wires into a compound. Then, in step 13, the sealing material may be attached to the sensor, and the cover closes the interior in step 12. Alternatively, in step 14 the sealing material is attached to the cover, and the interior is closed by the cover in step 12. The process steps may be executed in the suggested sequence. However, variations are possible: For example, the sealing material may be attached to the sensor prior to electrically connecting the sensor to the support. In case of attaching the sealing material to the cover, this step may be executed independent from all the other steps as the cover can be prefabricated including the sealing material.

The step of closing the interior by means of the cover with the cover holding the opening always includes aligning the opening in the cover with the sensor on the support.

The present invention is not limited to the application of humidity sensing. The sensor may be any sensor for measuring a quantity of a measure in an environment of the sensor. Insofar, the sensor may be a liquid or gas flow sensor, a pressure sensor, a chemical sensor or an infrared sensor. For the first one of these applications, it is preferred that the seal between the sensor and the opening is a liquid-tight seal, for the second one of these applications it is preferred that the seal is a gas-tight seal.

While there are shown and described presently preferred embodiments of the invention, it is to be distinctly understood that the invention is not limited thereto but may be otherwise variously embodied and practiced within the scope of the following claims.

The invention claimed is:

1. Sensing device, comprising
a sensor for providing sensor data representative of a quantity to be measured,
a radio frequency interface for transmitting the sensor data,
a casing for the sensor and the radio frequency interface, the casing comprising an opening for exposing a sensitive element of the sensor to an environment of the casing, and
a seal for sealing the opening against an interior of the casing,
wherein the casing comprises a support for the sensor, the support comprising conductor paths for electrically connecting the sensor to the radio frequency interface,
wherein the casing comprises a cover, and
wherein the cover includes the opening, and wherein the seal is arranged between the sensor and the cover.

2. Sensing device according to claim 1, wherein the support is built from a plastic foil with one or both of the conductor paths and an antenna of the radio frequency interface being arranged on the foil.

3. Sensing device according to claim 1, wherein the radio frequency interface comprises an interface chip which interface chip is flip chip mounted to the support.

4. Sensing device according to claim 1,
wherein the cover is built from a flexible foil made from plastics, and wherein a periphery of the cover is attached to a periphery of the support.

5. Sensing device according to claim 1, wherein the sensor chip comprises through-silicon vias for electrically connecting electronic components arranged next to the sensitive element at one side of the sensor chip to contact pads for electrically contacting the sensor chip to the support arranged at an opposite side of the sensor chip.

6. Sensing device according to claim 1, wherein the sensor is electrically connected to the support by means of bond wires, and wherein the interior of the casing is at least partially filled by a compound.

7. Sensing device according to claim 1, comprising means for deriving energy from a signal received by an antenna of the radio frequency interface for operating the sensor.

8. Sensing device according to claim 1, wherein the seal is one of a liquid-tight and a gas-tight seal, and wherein the sensor is one of a humidity sensor and a pressure sensor, a flow sensor, a chemical sensor and an infrared sensor.

9. Method for manufacturing a sensing device, comprising the steps of
arranging a sensor for providing sensor data representative of a quantity to be measured and a radio frequency interface for transmitting the sensor data on a support of a casing for the sensor and for the radio frequency interface,
providing a seal for sealing an opening of the casing for exposing a sensitive element of the sensor to an environment against an interior of the casing, and
closing the interior with a cover,
wherein the support comprises conductor paths for electrically connecting the sensor to the radio frequency interface,
wherein the casing includes the cover,
wherein the cover includes the opening, and
wherein the seal is arranged between the sensor and the cover.

10. Method of claim 9, comprising the step of arranging the seal at one of the sensor and the cover, and closing the casing with the cover such that the sensitive element faces the opening.

* * * * *